United States Patent [19]

Cormier

[11] 4,377,577

[45] Mar. 22, 1983

[54] USE OF PSYCHOACTIVE DRUGS IN UTERUS TO PREVENT PREGNANCY

[75] Inventor: Milton J. Cormier, Bogart, Ga.

[73] Assignee: University of Georgia Research Foundation, Inc., Athens, Ga.

[21] Appl. No.: 253,567

[22] Filed: Jul. 6, 1981

Related U.S. Application Data

[63] Continuation-in-part of Ser. No. 155,800, May 30, 1980.

[51] Int. Cl.³ .................... A61K 31/38; A61K 31/54; A61K 31/495
[52] U.S. Cl. .................................. 424/247; 424/252; 424/267; 424/275; 424/330; 424/331; 424/DIG. 14
[58] Field of Search ................ 424/247, 267, 275, 250

[56] References Cited

U.S. PATENT DOCUMENTS 2,541,103 2/1951 Sander .................... 424/DIG. 14 X

OTHER PUBLICATIONS

Chemical Abstracts 82:11065u, 1975.
Chemical Abstracts 82:25709u, 1975.
Chemical Abstracts 72:130759b, 1970.
Physicians Desk Reference (PDR), 26th ed. 1972, pp. 909 & 910, 1292 & 1293.

*Primary Examiner*—Leonard Schenkman
*Attorney, Agent, or Firm*—Sumner C. Rosenberg

[57] ABSTRACT

The use of psychoactive drugs by injecting or introducing such drugs directly into the uterus is disclosed as a means of preventing pregnancy after intercourse has occurred. Various means of introducing such drugs are disclosed, such as by mixing such psychoactive drugs with jelly carriers, foam carriers, or paraffin oil.

8 Claims, No Drawings

USE OF PSYCHOACTIVE DRUGS IN UTERUS TO PREVENT PREGNANCY

This application is a continuation-in-part of Application Ser. No. 155,800 filed May 30, 1980.

The present invention relates to a method of preventing pregnancy. More specifically, the present invention relates to the use of calmodulin binding drugs as a means to prevent pregnancy after intercourse by injecting such drugs into the uterus.

Presently, there is no effective method or product known for preventing conception or pregnancy after sexual intercourse has occurred, especially after an hour or more has elapsed after intercourse. For the purpose of this application pregnancy is intended to be defined as the implantation of a fertilized egg to the uterus.

Currently, in cases of rape or other cases of intercourse where pregnancy is unwanted, other than using douches or other normally ineffective methods to attempt to prevent conception, the normal practice is to wait to see whether the signs of pregnancy occur and, if so, have an abortion if the pregnancy is to be terminated.

Drugs that are capable of binding with calmodulin only in the presence of calcium are known as calmodulin binding drugs. Psychoactive drugs constitute one class of calmodulin binding drugs. Other known calmodulin binding drugs are disclosed in this application.

Psychoactive drugs are currently used clinically to treat certain types of mental disorders and stress. Chemical classes of psychoactive drugs and examples of drugs in each class are as follows:

| Chemical Class | Examples |
| --- | --- |
| Phenothiazines | Trifluoperazine |
| | Fluphenazine |
| | Thioridazine |
| | Chlorpromazine |
| | Promethazine |
| Thioxanthenes | Chlorprothixene |
| Butyrophenones | Penfluridol |
| | Benperidol |
| | Haloperidol |
| Diphenylbutylamines | Pimozide |
| Dibenzodiazepines | Clozapine |
| Benzodiazepines | Medazepam |
| | Chlordiazepoxide |
| Dibenzazepines | Imipramine |
| | Amitriptyline |
| | Protriptyline |
| | Desipramine |

The use of psychoactive drugs as medications to affect mental processes has become widespread since the early 1950's. Such use typically entails taking such drugs internally at dosages ranging from 10 to 120 milligrams daily. For a detailed background of such use and description of such drugs see Chapter 12 of *The Pharmacological Basis of Theraputics*, 5th Ed., edited by L. S. Goodman and A. Gilman (1975).

DESCRIPTION OF THE INVENTION

The present invention comprises the use of calmodulin binding drugs to prevent pregnancy. The introduction of such drugs into the uterus can be accomplished by normal clinical methods, such as injection by way of the vaginal tract, through the cervix and into the uterus. Such treatment is quick and simple; at least as simple as the currently used procedure for PAP Smears. By injection of an effective amount or concentration of one or a combination of calmodulin binding drugs into the uterus prior to the implantation of a fertilized egg to the wall of the uterus, pregnancy will be prevented. Calmodulin binding drugs in the uterus will either prevent conception, if it has not yet taken place, or embryonic development of a fertilized egg prior to and necessary for implantation. Since implantation normally does not occur for several days after conception, the present invention may be used effectively for a significant period of time after intercourse, perhaps up to three or four days later.

The present invention does not involve the killing of the sperm, but instead directly and specifically blocks the physiological process of conception and embryonic development. It has been shown in the past few years that there is a regulatory protein known as calmodulin, found in all cells of higher organisms and which is the key to the control of a wide variety of physiological processes. We have found that calmodulin is involved in triggering the activation of mammalian spermatozoa, a prerequisite to the fertilization process, as well as in triggering the early events of ovum development after fertilization has occurred. Calmodulin is a calcium binding protein, which means that when calcium is bound to the protein the resulting calcium-protein complex turns on a variety of cellular processes including spermatozoan or ovum activation. We have found that calmodulin binding drugs inhibit the calmodulin function, and, as a result, use of such drugs will prevent the activation of spermatozoa and will prevent embryonic development following fertilization.

It is known that psychoactive drugs will bind tightly to calmodulin only in the presence of calcium. The binding of these drugs to calmodulin results in the inhibition of calmodulin function. We have found that of the many thousands of proteins found in a cell, calmodulin is the only detectable target of psychoactive drugs. Thus, psychoactive drugs are specific in their binding to calmodulin and will specifically inhibit calmodulin function.

The use of a psychoactive drug in the uterus to prevent pregnancy has a number of advantages. First, it is extremely effective since the specific binding of the drug to calmodulin would turn off spermatozoan or ovum activation and embryonic development and thus prevent pregnancy. Experimental evidence has demonstrated that the phenothiazine drugs penetrate the spermatozoan membranes within seconds and concentrate in the region of the cell occupied by calmodulin. Second, there will be no expected side effects since the drug would not be used internally and since low concentrations will be very effective. Third, the effectiveness of an application may last for hours due to the stability of these drugs.

Other known calmodulin binding drugs include the following two classes of compounds. The first class includes, and is exemplified by the following compounds:
 (a) 8-anilino-1-naphthalenesulfonate
 (b) 9-anthroylcholine
 (c) N-phenyl-1-naphthylamine The second class of compounds includes, and is exemplified by the following compounds:
 (a) N-(6 aminohexyl)-5-chloro-1-naphthalenesulfonamide
 (b) N-(6 aminohexyl)-5-chloro-2-naphthalenesulfonamide (c) N-(6 aminohexyl)-5-bromo-2-naphthalenesulfonamide The most effective drugs can be predicted based on their effectiveness in binding to calmodulin. Therefore, the most promising specific psychoactive drugs, in order of effectiveness, are: penfluridol, pimozide, trifluoperazine, fluphenazine, chlorprothixene, thioridazine, chlorpromazine, benperidol, haloperidol, and clozapine.

To accomplish the present invention the calmodulin binding drugs would be combined with an appropriate carrier medium, such as paraffin oil, foam carriers or jelly carriers.

A preferred embodiment of the present invention comprises a buffered two percent concentration of trifluoperazine in paraffin oil, introduced into the uterus in sufficient quantity and under known methods within six hours after sexual intercourse has occurred and allowed to remain therein.

What is claimed is:

1. The method of preventing pregnancy which comprises introducing an effective amount of a psychoactive drug directly into the uterus of the female.

2. The method as described in claim 1, wherein the step of introducing said psychoactive drug comprises introducing said psychoactive drug and a foam carrier directly into the uterus of the female after sexual intercourse by injection means.

3. The method as described in claim 1, wherein the step of introducing said psychoactive drug comprises introducing a mixture of said psychoactive drug and a jelly carrier directly into the uterus of the female after sexual intercourse by injection means.

4. The method as described in claim 1, wherein the step of introducing said psychoactive drug comprises introducing a mixture of said psychoactive drug and paraffin oil directly into the uterus of the female after sexual intercourse by injection means.

5. The method as described by claims 1, 2, 3 or 4, wherein said psychoactive drug is selected from the group consisting of the phenothiazines, thioxanthenes, butyrophenones, diphenylbutylamines, dibenzodiazepines, benzodiazepines, and dibenzazepines.

6. The method as described by claims 1, 2, 3 or 4, wherein said psychoactive drug is selected from the group consisting of penfluridol, pimozide, trifluoperazine, flophenazine, chloroprothixene, thioridazine, benperidol, haloperidol, and clozapine.

7. The method as described by claim 6, wherein the amount of the psychoactive drug introduced into the uterus is about 10 milligrams or greater.

8. The method as described by claims 1, 2, 3, or 4, wherein said injection means is accomplished by way of the vaginal tract, through the cervix and into the uterus.

* * * * *